United States Patent
Rollat et al.

(10) Patent No.: US 7,655,305 B2
(45) Date of Patent: Feb. 2, 2010

(54) ADHESIVE NONSPHERICAL MICRO-OBJECTS FOR STYLING AND/OR MAKING UP THE HAIR

(75) Inventors: Isabelle Rollat, Paris (FR); Henri Samain, Bievres (FR)

(73) Assignee: L'Oreal S.A., Paris (FR)

(*) Notice: Subject to any disclaimer, the term of this patent is extended or adjusted under 35 U.S.C. 154(b) by 855 days.

(21) Appl. No.: 10/917,278

(22) Filed: Aug. 13, 2004

(65) Prior Publication Data
US 2005/0079207 A1 Apr. 14, 2005

(30) Foreign Application Priority Data
Aug. 13, 2003 (FR) .................................. 03 09917

(51) Int. Cl.
*B32B 5/16* (2006.01)
(52) U.S. Cl. .................. 428/407; 428/212; 428/500
(58) Field of Classification Search ................. 428/403, 428/407, 212, 500
See application file for complete search history.

(56) References Cited

U.S. PATENT DOCUMENTS

| | | | | |
|---|---|---|---|---|
| 4,963,348 | A * | 10/1990 | Bolich et al. | 424/70.12 |
| 5,019,377 | A * | 5/1991 | Torgerson | 424/70.16 |
| 5,441,728 | A | 8/1995 | Tsaur et al. | |
| 6,346,234 | B1 | 2/2002 | Rollat et al. | |
| 6,548,051 | B2 * | 4/2003 | Garnier et al. | 424/70.1 |
| 6,689,346 | B1 * | 2/2004 | Rollat et al. | 424/70.1 |
| 7,048,916 | B2 * | 5/2006 | Rollat et al. | 424/70.1 |
| 2002/0041858 | A1 | 4/2002 | Garnier et al. | |
| 2003/0143180 | A1 | 7/2003 | Giroud et al. | |
| 2003/0161804 | A1 | 8/2003 | Perron et al. | |
| 2004/0001798 | A1 | 1/2004 | Perron et al. | |
| 2006/0024255 | A1 * | 2/2006 | Quadir et al. | 424/70.1 |
| 2008/0124296 | A1 * | 5/2008 | Elmasry et al. | 424/70.19 |

FOREIGN PATENT DOCUMENTS

| | | |
|---|---|---|
| EP | 1 072 650 A1 | 1/2002 |
| FR | 2 811 886 | 1/2002 |
| FR | 2 833 959 | 6/2003 |
| FR | 2 833 960 | 6/2003 |
| JP | 07-157672 * | 6/1995 |
| WO | WO 98/38969 | 9/1998 |
| WO | WO 98/38969 A2 * | 9/1998 |
| WO | WO 01/00150 A1 | 1/2001 |
| WO | WO 01/21142 A1 | 3/2001 |

OTHER PUBLICATIONS

French Search Report FR 0309917 (French priority application for the present application) dated Apr. 27, 2004.
Database WPI Week 199533, Derwent Publications Ltd., London, GB; An 1995-252428, XP002278202 & JP 07 157672 A, Jun. 20, 1995.
English Language Derwent Abstract for WO 01/00150 A1; Derwent Week 200115, dated Jan. 4, 2001.
English Language Derwent Abstract for WO 01/21142 A1; Derwent Week 200135, dated Mar. 29, 2001.
Material Safety Data Sheet for GEL-TAC® 100B, dated Dec. 24, 2002.
Merck Analysenzertifikat for Timiron® Splendid Violet, dated Apr. 26, 2000.
English Translation for Merk Analysenzertifikat for Timiron® Splendid Violet, translation date Feb. 19, 2009.

* cited by examiner

*Primary Examiner*—H. (Holly) T Le
(74) *Attorney, Agent, or Firm*—Finnegan, Henderson, Farabow, Garrett & Dunner, L.L.P.

(57) ABSTRACT

The disclosure relates to adhesive nonspherical microobjects ranging from 1 to 1,000 μm in size and comprising at least one adhesive organic polymer, a method of styling and/or making up keratinous fibers comprising applying to the keratinous fibers such microbjects, and to cosmetic compositions comprising such microbjects.

20 Claims, No Drawings

ADHESIVE NONSPHERICAL MICRO-OBJECTS FOR STYLING AND/OR MAKING UP THE HAIR

The present disclosure relates to adhesive nonspherical microobjects, a method of styling and/or making up keratinous fibers comprising applying to the keratinous fibers such microobjects, and to cosmetic compositions comprising such microobjects.

There are numerous styling products on the market in the form of lacquers, sprays, gels or lotions. These products are solutions or dispersions of polymers which, after evaporation of the solvent phase, provide for the fixing and form retention of a hairstyle by virtue of the formation of polymer films surrounding each hair in the manner of a sheath and by virtue of the establishment of physical bonds between the hairs.

This type of fixing of the hairstyle is definitive since any significant modification of the shape of the hairstyle irreversibly severs the connections and consequently detrimentally affects the form retention of the hairstyle. Conventional styling products therefore do not make possible remodelling of the hairstyle without the introduction of an additional styling product.

One approach for developing compositions which make possible the restyling or remodelling of the hair without addition of material involves combining, with conventional fixing polymers, at least one hot-melt polymer with a low melting point. When the polymer layer is heated, plasticization of the polymer layer results, so that the hair can be remodelled to a new shape. The new shape is then fixed by simple cooling (see French Patent Application FR 2,811,886).

Another approach involves depositing on the hair adhesive and/or self-adhesive fixing polymers in the form of films (see WO 98/38969) or particles (see U.S. Patent Publication No. 2002/0041858). The adhesive bonds thus established between the keratinous fibers make possible, depending on the tackiness of the coats formed, strong or flexible fixing of the hair, such as reversible fixing, i.e., the form retention of a shape which may be modified at any time by simply passing the hand through the hair or using an appropriate implement.

The present inventors, in the context of their research regarding the deposition of adhesive particles for the purpose of reversible fixing and remodelling of the hair, have discovered that it is possible to obtain, in addition to the styling effect described above, highly advantageous decorative optical effects by choosing, among all the existing or conceivable adhesive particles, only nonspherical particles, that is to say particles having a shape such that the appearance of the particle varies according to the direction viewed.

These particles will be subsequently referred to herein as "nonspherical microobjects".

Disclosed herein, therefore, is an adhesive nonspherical microobject having a size ranging from 1 to 1,000 μm and comprising at least one adhesive organic polymer.

Another embodiment of the disclosure relates to an adhesive nonspherical microobject ranging from 1 to 1,000 μm in size and comprising at least one optionally noncoalescent solid phase covered, over at least a part of its surface, with at least one adhesive organic polymer.

When coverage is partial, the at least one solid phase is noncoalescent.

In another embodiment, the microobjects are composed solely of at least one adhesive polymer.

Another subject of the present disclosure is a method for styling and/or making up keratinous fibers, such as the hair, comprising applying to the keratinous fibers the adhesive nonspherical microobjects disclosed herein.

Also disclosed herein are cosmetic compositions for styling and/or making up keratinous fibers, such as the hair, comprising the adhesive nonspherical micro-objects disclosed herein dispersed in a cosmetically acceptable liquid medium.

The microobjects disclosed herein adhere to the surface of the hairs and thus make it possible to cause the keratinous fibers to stick to one another. As for known adhesive particles, for example, disclosed in U.S. Patent Publication No. 2002/0041858, this adhesion is reversible and, for this reason, makes it possible to restyle the hair.

However, the micro-objects disclosed herein contribute an additional effect related to their nonspherical shape, the adjective "nonspherical" in this instance encompassing all the shapes which might be described as "anisotropic", that is to say all shapes exhibiting to the eye, in contrast to the spherical shape, a different appearance depending on the direction considered. This variation in the appearance as a function of the relative position of the eye with respect to the microobject makes it possible to obtain varied and highly original decorative effects. Depending on the shape, the size, the absorbance or the reflectance of the microobjects used, glossy, pearlescent or moiré effects may be, for example, observed.

The present inventors have found that the optical effects obtained following the immobilization of the microobjects disclosed herein at the surface of the hairs are particularly advantageous when the nonspherical microobjects have a shape exhibiting at least one or flat face and/or at least one curved face. Mention may be made, as examples of such microobjects, of tetrahedra, cubes, parallelepipeds, pyramids, prisms, sheets, cylinders, cones, truncated cones and concave and convex lenses.

In one embodiment, the microobjects have at least one flat surface, for example at least two flat surfaces.

In addition, these microobjects may, for example, have a shape exhibiting at least one plane, axis or centre of symmetry.

In another embodiment, the microobjects comprise at least one, optionally noncoalescent, solid phase. The term "noncoalescent phase" or "noncoalescent particle" is understood to mean, in the present disclosure, particles which, after deposition on the keratinous fiber and evaporation of the liquid dispersing phase, remain in a highly separated form without forming a continuous or noncontinuous film with the adjacent particles. In the state of the art, such materials or particles are also known as non-film-forming or not able to form a film.

The fact that the solid phase forming the support for the adhesive polymer does not coalesce after deposition on the hairs is an advantage for the present disclosure. This is because the microobjects have to retain their specific shape as much as possible for the desired optical effect.

From this viewpoint, it may be advisable to take care that the layer of adhesive polymer does not "hide" the specific shape of the solid phase, that is to say that the amount of adhesive polymer is not excessively larger than the volume of the noncoalescent solid phase.

The present inventors have found that an adhesive polymer/noncoalescent solid phase ratio by volume ranging from 0.02 to 1.0, for example from 0.05 to 0.8, may make it possible to guarantee sufficient adhesion of the particles to the keratinous fibers without masking the specific geometric shape of the solid phase.

As disclosed herein, it is not necessary, in general, for the entire surface of the microobjects to be covered by the layer of adhesive polymer. The proportion of surface covered by the adhesive polymer layer may be, for example, sufficient to make possible not only the adhesion of the microobjects disclosed herein to the treated keratinous fiber, but also the adhesion of the same immobilized microobject to a second keratinous fiber or optionally to a second microobject immobilized on a second fiber.

In one embodiment of the microobjects of the present disclosure, all or virtually all of the surface of the solid part is covered by the adhesive polymer.

However, the amount of adhesive polymer deposited or fixed to the surface of the noncoalescent solid phase of the microobjects of the present disclosure may also be just sufficient to cause the microobjects to adhere to the surface of the fiber without the establishment of adhesive bonds between different keratinous fibers. This will be the case, for example, when a single flat face of the microobjects is covered by a layer of adhesive polymer.

The styling effect of such microobjects will then be very slight, indeed even nonexistent, and the treatment of the keratinous fibers with such microobjects will then serve mainly for making up the fibers.

Such not very adhesive microobjects and a method of making up keratinous fibers comprising applying them to the keratinous fibers are also encompassed by the present disclosure.

The optionally noncoalescent solid phase of the microobjects disclosed herein can be organic or inorganic in nature. Mention may be made, as examples of inorganic materials which can be used for the noncoalescent solid phase, of metals and metal alloys, metal oxides, carbides and nitrides, ceramic materials and inorganic glasses.

When the optionally noncoalescent solid phase is an organic phase, it is generally an organic polymer. In order to be noncoalescent, this polymer has to be in the glassy state, that is, with a glass transition temperature significantly higher than the ambient temperature or the temperature of use (for example, the temperature of the human body), and/or has to be crosslinked.

The glass transition temperature of the organic polymers which can be used for the solid phase may be, for example, greater than 40° C., such as greater than 60° C., and for further example ranging from 80° C. to 200° C.

Mention may be made, among these polymers, in a nonexhaustive fashion, of polystyrene, poly(vinyl acetate), poly(α-methylstyrene), poly(acrylamide), poly(acrylonitrile), poly(vinyl chloride), copolymers based on styrene and on a $C_1$-$C_4$ alkyl (meth)acrylate, copolymers based on styrene and on acrylamide, copolymers based on styrene and on acrylonitrile, copolymers based on styrene and on vinyl acetate, copolymers based on acrylamide and on a $C_1$-$C_4$ alkyl (meth)acrylate, copolymers based on acrylonitrile and on a $C_1$-$C_4$ alkyl (meth)acrylate, copolymers based on acrylonitrile and on acrylamide, terpolymers based on styrene, on acrylonitrile and on acrylamide, poly(methyl methacrylate), poly(ethyl methacrylate) and styrene/butadiene, styrene/acrylic acid, styrene/vinylpyrrolidone and butadiene/acrylonitrile copolymers.

The optionally noncoalescent solid phase of the microobjects disclosed herein carries, over a part or all of its surface, a layer of adhesive organic polymer.

The adhesive polymer can be immobilized at the surface of the optionally noncoalescent solid phase by covalent chemical bonds (grafting) or by weak physicochemical interactions, such as hydrophobic interactions, hydrogen bonds and van der Waals forces (adsorption).

In another embodiment, the microobjects consist essentially of at least one adhesive organic polymer.

The adhesive nature of an organic polymer is generally related to its glass transition temperature. Polymers with a glass transition temperature ($T_g$) significantly lower than ambient temperature or the temperature of use tend to be adhesive. The adhesive organic polymers used for the preparation of the microobjects disclosed herein may have a glass transition temperature. for example, of less than or equal to 10° C., such as less than or equal to 0° C.

The adhesive organic polymers disclosed herein may have a self-adhesiveness, for example, such that the tensile force ($F_{max}$ (in N)) necessary to separate two surfaces coated with the polymer is greater than 1N, such as greater than 3N and, for further example, greater than 5N. This tensile force $F_{max}$ is measured under the following conditions: two discs each having a surface area of 38 mm², made of a rigid, inert and nonabsorbent solid material, such as glass, are coated with a coat of the adhesive polymer to be tested. The polymer is deposited in an amount of 519 μg/mm² from a solution in an appropriate solvent. After evaporating the solvent at 22° C. for 24 hours under a relative humidity of 50%, the two coated surfaces of the discs are superimposed and the discs pressed against one another for 20 seconds at a pressure of 3 newtons using a Lloyd model LR5K extensometer.

The stuck discs are then pulled apart at a rate of 20 mm/minute, so as to separate them from one another, and the tensile force is continuously recorded. The maximum tensile force, recorded at the moment of the separation of the two surfaces, referred to as $F_{max}$, characterizes the self-adhesiveness of the polymer. The greater this force, the greater the self-adhesiveness of the polymer.

The adhesive polymers which can be used for the present disclosure can also be characterized by their adhesiveness to an inert material, such as glass. This adhesiveness can be expressed in the form of energy ($E_s$) supplied by the same extensometer (Lloyd model LR5K) to separate a surface with an area of 38 mm², coated, under the above conditions (519 mg/mm², drying for 24 hours at 22° C., 50% relative humidity), with an adhesive polymer, from a surface made of polished glass, after compression of these two surfaces for 30 seconds with a force of 3 newtons. As above, the pull rate is 20 mm/min.

This energy $E_s$, corresponding to the sum of the work supplied up to separation, can be calculated according to the following formula:

$$\int_{Xs1+0.05}^{Xs2} F(x)dx$$

where

F(x) is the force necessary to produce a displacement (x),

Xs1 is the displacement (expressed in mm) produced by the maximum tensile force, and Xs2 is the displacement (expressed in mm) produced by the tensile force which makes possible complete separation of the two surfaces.

For the adhesive polymers disclosed herein, the separation energy $E_s$ may be, for example, at most equal to 300 μJ, such as at most equal to 250 μJ.

The chemical nature of the adhesive organic polymers is not determinative for the present disclosure provided that the layer of polymer exhibits the above characteristics of adhesiveness and/or of self-adhesiveness. These adhesive polymers may or may not be crosslinked. The following applications all disclose adhesive particles or polymers that are useful herein: WO 98/38969, FR 2,833,960 (self-adhesive cationic or amphoteric polyurethanes), and FR 2,833,959 (self-adhesive cationic or amphoteric radical polymers).

The microobjects disclosed herein range from 1 µm to 1,000 µm, such as from 10 µm to 900 µm in size. This size is a measure of the greatest dimension of each microobject. It is clearly understood that, when a population of microobjects of different sizes is involved, the size indicated corresponds to the mean size of the population.

Another subject of the present disclosure is styling and/or make-up compositions for keratinous fibers. In these hair compositions, the microobjects are dispersed in a cosmetically acceptable liquid medium. The cosmetically acceptable liquid medium generally comprises water and/or at least one organic solvent commonly used in cosmetics. These cosmetically acceptable solvents are liquid at ambient temperature and atmospheric pressure. These solvents may be, for example, monoalcohols, polyols and ethers of these alcohols and polyols. Mention may be made, for example, of ethanol, isopropanol, glycerol, propylene glycol and propylene glycol monomethyl ether.

This liquid medium should, of course, be chosen so as not to dissolve the adhesive organic polymer and the solid phase.

The concentration of the microobjects in the hair compositions disclosed herein ranges, for example, from 1 to 90% by weight, such as from 1 to 80% by weight, and for further example from 1 to 50% by weight, with respect to the total weight of the composition.

The hair compositions disclosed herein can additionally comprise cosmetic active principles and adjuvants commonly used in the hair field. These additives are chosen, for example, from vitamins, amino acids, oligopeptides, peptides, hydrolyzed and nonhydrolyzed and modified and unmodified proteins, enzymes, branched and unbranched fatty acids and alcohols, animal, vegetable and mineral waxes, ceramides and pseudoceramides, hydroxylated organic acids, UV screening agents, antioxidants and agents for combating free radicals, chelating agents, antidandruff agents, seborrhoea-regulating agents, soothing agents, cationic, anionic, nonionic and amphoteric surface-active agents, cationic, anionic, neutral or amphoteric polymers, organomodified and nonorganomodified silicones, mineral, vegetable and animal oils, polyisobutenes and poly(α-olefin)s, fatty esters, and coloring agents, such as pigments and direct dyes.

The microobjects disclosed herein can be prepared according to any appropriate process which makes possible the manufacture of such objects of small size having a specific shape.

In one embodiment, the optionally noncoalescent solid phase can be prepared, for example, by casting a thin film from a solution of a polymer, drying and cutting up this film with an appropriate implement, such as a laser beam, a blade or a punch. The polymer film can also be subjected to a heating or irradiating stage for the purpose of crosslinking it.

The adhesive polymer layer can be applied to the film before cutting, for example by spraying, immersing, centrifuging or spreading by a roller or a doctor blade. The adhesive polymer coat may also be deposited on the microobjects after cutting up the film. This application can be carried out, for example, by spraying or immersing.

The optionally noncoalescent solid phase, can also be prepared by extrusion, from a polymer in the molten state or from a polymer solution having an appropriate viscosity, of sheets or very fine strands with a circular or polygonal cross section. These strands or sheets may then subsequently be cut up to produce the microobjects according to the disclosure. The coat of adhesive polymer can be applied to the noncoalescent solid phase in the way described above or alternatively by coextrusion of the adhesive polymer and the polymer forming the noncoalescent solid phase.

In another embodiment, the adhesive polymer can be polymerized in situ and can be cut up according to the desired shapes by the same techniques as described above.

Other than in the operating example below, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. The following example is intended to illustrate the disclosure without limiting the scope as a result.

EXAMPLE 1

Composition According to the Present Disclosure

| | |
|---|---|
| Sheet-like polystyrene particles completely covered with polymer AQ ™ 1350* (20 µm × 5 µm) | 2 g |
| Crosslinked polyacrylic acid | 0.3 g |
| Water | q.s. 100 g |

*water-dispersible branched sulphonated polyester sold by Eastman Chemical Company The polystyrene can be replaced by boron nitride.

What is claimed is:

1. An adhesive nonspherical microobject having a size ranging from 1 to 1,000 µm and comprising at least one noncoalescent solid phase covered, over at least a part of its surface, with at least one adhesive organic polymer; wherein the noncoalescent solid phase comprises at least one organic polymer having a class transition temperature greater than 40° C. chosen from polystyrene, poly(vinyl acetate), poly(methylstyrene), poly(acrylamide), poly(acrylonitrile), poly(vinyl chloride), copolymers based on styrene and on a $C_1$-$C_4$ alkyl (meth)acrylate, copolymers based on styrene and on acrylamide, copolymers based on styrene and on acrylonitrile, copolymers based on styrene and on vinyl acetate, copolymers based on acrylamide and on a $C_1$-$C_4$ alkyl (meth)acrylate, copolymers based on acrylonitrile and on a $C_1$-$C_4$ alkyl (meth)acrylate, copolymers based on acrylonitrile and on acrylamide, terpolymers based on styrene, on acrylonitrile and on acrylamide, poly(methyl methacrylate), poly(ethyl methacrylate) and styrene/butadiene, styrene/acrylic acid, styrene/vinylpyrrolidone and butadiene/acrylonitrile copolymers.

2. The adhesive nonspherical microobject according to claim 1 wherein the at least one adhesive organic polymer has a glass transition temperature (Tg) less than 10° C.

3. The adhesive nonspherical microobject according to claim 2, wherein the at least one adhesive organic polymer has a glass transition temperature (Tg) less than 0° C.

4. The adhesive nonspherical microobject according to claim 1, wherein the at least one adhesive organic polymer has a self-adhesiveness such that the tensile force necessary to separate two surfaces coated with the polymer is greater than 1N.

5. The adhesive nonspherical microobject according to claim 4 wherein the at least one adhesive organic polymer has a self-adhesiveness such that the tensile force necessary to separate two surfaces coated with the polymer is greater than 3N.

6. The adhesive nonspherical microobject according to claim 1, wherein the at least one adhesive organic polymer has an adhesiveness such that the energy supplied to separate a surface with an area of 38 $mm^2$ coated with the polymer from a surface made of polished glass is less than 300 µJ.

7. The adhesive nonspherical microobject according to claim 1 wherein the microobject has a shape exhibiting at least one flat face.

8. The adhesive nonspherical microobject according to claim 7, wherein the microobject has a shape exhibiting at least one flat face and at least one curved face.

9. The adhesive nonspherical microobject according to claim 7, wherein the microobject has a shape exhibiting at least two flat faces.

10. The adhesive nonspherical microobject according to claim 7, wherein the microobject has the shape of a tetrahedron, of a cube, of a parallelepiped, of a pyramid, of a prism, of a sheet, of a cylinder, of a cone, or of a truncated cone.

11. The adhesive nonspherical microobject according to claim 1, wherein the microobject has a shape exhibiting at least one curved face.

12. The adhesive nonspherical microobject according to claim 11, wherein the microobject has the shape of a cone, of a cylinder, of a concave lens, or of a convex lens.

13. The adhesive nonspherical microobject according to claim 1, wherein the microobject exhibits at least one centre, axis or plane of symmetry.

14. The adhesive nonspherical microobject according to claim 1, wherein the at least one solid phase further comprises an inorganic material chosen from metals, metal alloys, metal oxides, carbides, nitrides, ceramic materials and mineral glasses.

15. The nonspherical microobject according to claim 1, wherein the solid phase comprises at least one organic polymer having a glass transition temperature ranging from 80° C. to 200° C.

16. The nonspherical microobject according to claim 1, wherein that the at least one solid phase comprises at least one crosslinked organic polymer.

17. The nonspherical microobject according to claim 1, wherein the at least one adhesive polymer covers all or virtually all of the surface of said microobject.

18. The nonspherical microobject according to claim 1, wherein the at least one adhesive polymer is fixed to the solid phase by covalent chemical bonds and/or by weak physicochemical interactions, and wherein the weak physicochemical interactions are chosen from hydrophobic interactions, hydrogen bonds, and van der Waals forces.

19. The nonspherical microobject according to claim 1, wherein the ratio by volume of the at least one adhesive polymer to the solid phase ranges from 0.02 to 1.0.

20. The nonspherical microobject according to claim 19, wherein the ratio by volume of the at least one adhesive polymer to the solid phase ranges from 0.05 to 0.8.

* * * * *